United States Patent
Gonzalez

(10) Patent No.: US 12,290,634 B2
(45) Date of Patent: *May 6, 2025

(54) AIRWAY MASK INTERFACE APPARATUS

(71) Applicant: Henry Gonzalez, Upland, CA (US)

(72) Inventor: Henry Gonzalez, Upland, CA (US)

(*) Notice: Subject to any disclaimer, the term of this patent is extended or adjusted under 35 U.S.C. 154(b) by 843 days.

This patent is subject to a terminal disclaimer.

(21) Appl. No.: 17/386,128

(22) Filed: Jul. 27, 2021

(65) Prior Publication Data

US 2021/0353891 A1    Nov. 18, 2021

(51) Int. Cl.
*A61M 16/06*    (2006.01)
*A61M 16/12*    (2006.01)
*A61M 16/20*    (2006.01)

(52) U.S. Cl.
CPC .... *A61M 16/0605* (2014.02); *A61M 16/0666* (2013.01); *A61M 16/20* (2013.01); *A61M 16/0622* (2014.02); *A61M 16/122* (2014.02); *A61M 2205/12* (2013.01)

(58) Field of Classification Search
CPC .......... A61M 16/0605; A61M 16/0666; A61M 16/06; A61M 16/0611; A61M 16/0616; A61M 16/0622; A61M 16/0627; A61M 16/0633; A61M 16/0644; A61M 16/065; A61M 16/0655; A61M 16/0672; A61M 2205/12; A61M 16/14

See application file for complete search history.

(56) References Cited

U.S. PATENT DOCUMENTS

| | | |
|---|---|---|
| 2,376,871 A | 5/1945 | Fink |
| 2,382,364 A | 8/1945 | Yant |
| 2,505,173 A | 12/1948 | Conley |
| 3,343,535 A | 9/1967 | Lytle |
| 3,841,319 A | 10/1974 | Michael |
| 3,915,173 A | 10/1975 | Brekke |
| 4,235,239 A | 11/1980 | Elam |
| 4,327,720 A | 5/1982 | Bronson |
| 4,739,755 A | 4/1988 | White |
| 4,770,169 A | 9/1988 | Schmoegner |
| 4,790,327 A | 12/1988 | Despotis |
| 4,995,388 A | 2/1991 | Brain |

(Continued)

FOREIGN PATENT DOCUMENTS

| | | |
|---|---|---|
| DE | 1142500 | 1/1963 |
| DE | 102017009391 A1 * | 4/2019 |

(Continued)

OTHER PUBLICATIONS

DE 102017009391 Machine translation (Year: 2019).*

*Primary Examiner* — Timothy A Stanis
*Assistant Examiner* — Sara K Toich
(74) *Attorney, Agent, or Firm* — Jafari Law Group Inc.

(57) ABSTRACT

An airway mask interface apparatus for administering gas to a person's respiratory system is provided. The invention acts as a membrane between the person's face and a gas producing mask and covers and forms to the person's facial features and to the contours of the gas producing mask. The interface includes a first conduit passing through the interface in the region of the user's mouth, and a second conduit passing from the first conduit to the region of the user's nose. In this way, gas delivered to the interface passes through the first and second conduits and into the user's respiratory system with minimal leakage.

19 Claims, 8 Drawing Sheets

(56) References Cited

U.S. PATENT DOCUMENTS

| | | |
|---|---|---|
| 5,067,497 A | 11/1991 | Greear |
| 5,074,297 A | 12/1991 | Venegas |
| 5,197,463 A | 3/1993 | Jeshuran |
| 5,201,310 A | 4/1993 | Turnbull |
| 5,241,956 A | 9/1993 | Brain |
| 5,277,178 A | 1/1994 | Dingley |
| 5,647,357 A | 7/1997 | Barnett |
| 6,196,223 B1 | 3/2001 | Belfer |
| 6,631,718 B1 | 10/2003 | Lovell |
| 6,981,502 B2 | 1/2006 | McCormick |
| 7,007,696 B2 | 3/2006 | Palkon |
| 8,166,967 B2 | 5/2012 | Qiu |
| 8,336,549 B2 | 12/2012 | Nashed |
| 8,360,062 B2 | 1/2013 | Berthon-Jones |
| 8,448,636 B2 | 5/2013 | Singh |
| 1,019,907 A1 | 4/2014 | Doshi |
| 10,322,312 B1 | 6/2019 | Danford |
| 11,273,274 B1 * | 3/2022 | Schatz ............ A61M 15/0085 |
| 2007/0125385 A1 * | 6/2007 | Ho .................. A61M 16/0683 |
| | | 128/206.26 |
| 2008/0210242 A1 * | 9/2008 | Burk .................. A61M 16/06 |
| | | 128/206.21 |
| 2012/0304999 A1 * | 12/2012 | Swift .................. A61M 16/06 |
| | | 128/205.25 |
| 2015/0013682 A1 * | 1/2015 | Hendriks ......... A61M 16/0644 |
| | | 29/592 |
| 2016/0367782 A1 | 12/2016 | Henry |
| 2018/0043121 A1 * | 2/2018 | Goulitski .......... A61M 16/0605 |
| 2020/0146875 A1 | 5/2020 | Radmand |
| 2021/0038848 A1 * | 2/2021 | Eves .............. A61M 16/0616 |

FOREIGN PATENT DOCUMENTS

| | | |
|---|---|---|
| GB | 1191793 | 5/1970 |
| WO | WO2019/223465 | 11/2019 |
| WO | WO2020/054932 | 3/2020 |

* cited by examiner

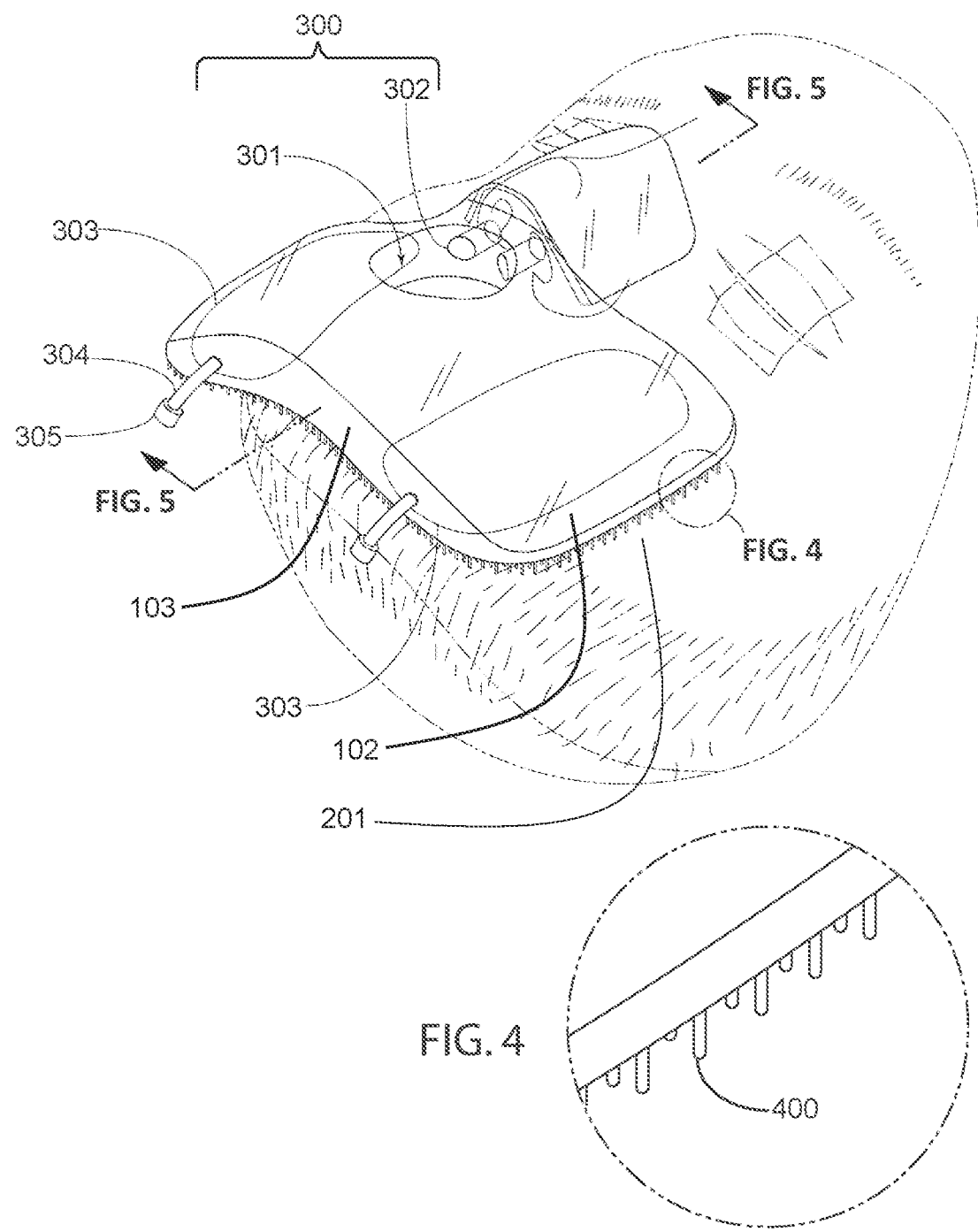

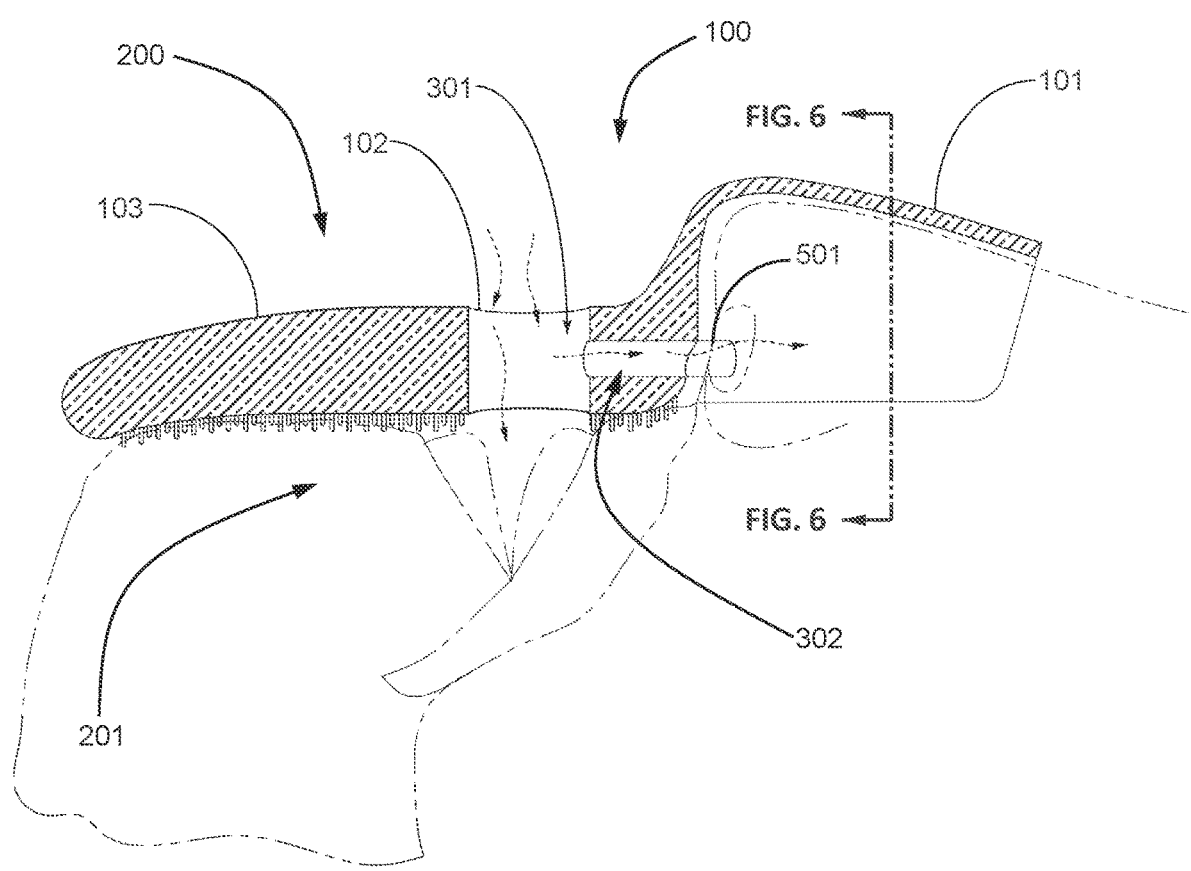

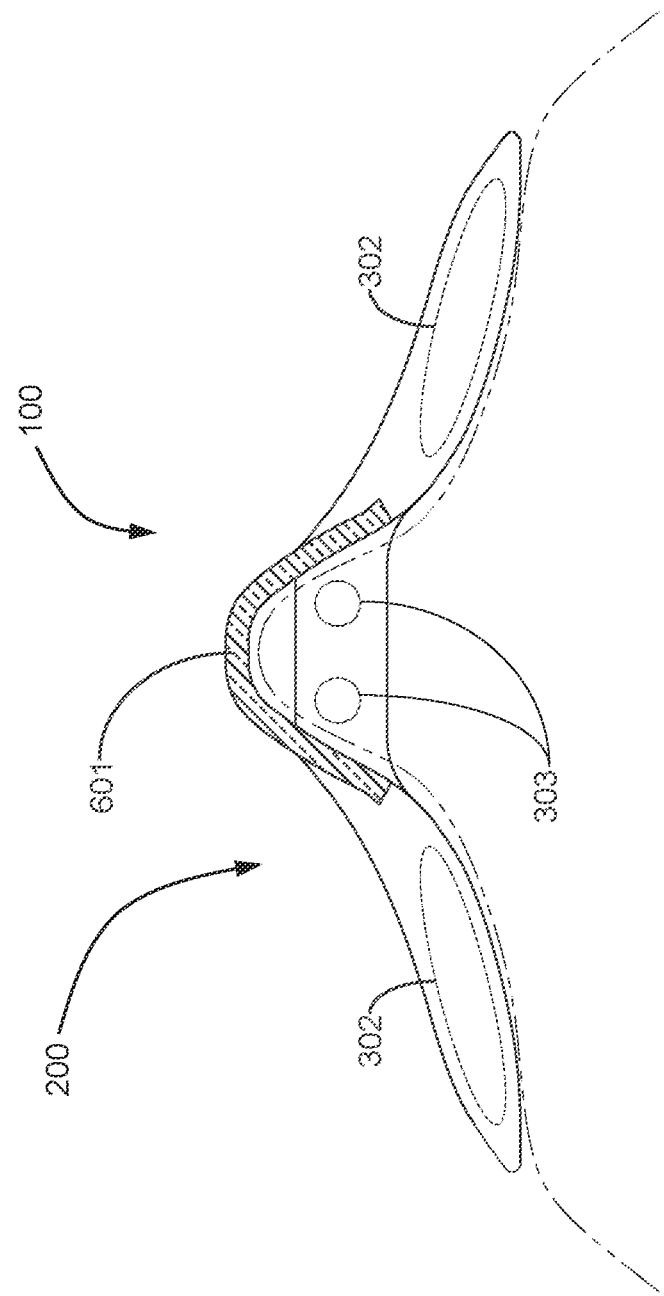

AIRWAY MASK INTERFACE APPARATUS

PRIORITY NOTICE

The present application claims priority under 35 U.S.C. § 119(e) to U.S. Provisional Patent Application Ser. No. 63/056,884 filed on Jul. 27, 2020, the disclosure of which is incorporated herein by reference in its entirety.

TECHNICAL FIELD OF THE INVENTION

The present disclosure relates generally to an airway device used to act as an interface between a gas producing mask and a person's face to create a proper sealing between the surfaces.

COPYRIGHT AND TRADEMARK NOTICE

A portion of the disclosure of this patent application may contain material that is subject to copyright protection. The owner has no objection to the facsimile reproduction by anyone of the patent document or the patent disclosure, as it appears in the Patent and Trademark Office patent file or records, but otherwise reserves all copyrights whatsoever. Certain marks referenced herein may be common law or registered trademarks of third parties affiliated or unaffiliated with the applicant or the assignee. Use of these marks is by way of example and should not be construed as descriptive or to limit the scope of this invention to material associated only with such marks.

BACKGROUND OF THE INVENTION

Gas producing masks such as the anesthesia gas mask are well known in the art. These devices are used to administer anesthetic gases or oxygen to a person through inhalation. The mask typically has an oval shape and fits over the mouth and nose of the person. The device has a double hose system where one hose carries inhaled anesthetic gas to the mask and the other brings exhaled anesthetic gas back to the gas producing machine. Anesthesia gas masks also have a gasket where it acts as a sealing mechanism between the mask and the face to prevent the produced anesthetic gas or oxygen from escaping. The gasket is usually comprised of an air cushion that covers the outer circumference of the mask and is pressed against the person's face to create a seal. Although the gasket volume can typically be adjusted through a valve that increases or decreases air in the gasket to better fit the person's face, it sometimes does not properly seal against the person's face, especially if the person has distinct facial features.

To solve the problem of the adjustability of the gasket to properly seal against a person's face, previous inventions have tried to integrate the solution with the gas producing mask itself. For example, U.S. Pat. No. 6,196,223 B1 discloses a respiratory facial mask with a moldable laminated gasket member having a cushioning layer and adhesive layer for engaging the facial contours of the skin of the wearer's face. Furthermore, U.S. Pat. No. 5,647,357 discloses a respiratory mask incorporating a gel substance possessing resilience characteristics corresponding to those of human fat tissue.

However, none of the previous inventions adequately address the improper fitting of the gas producing mask with the facial features of a person by implementing a separate interface that interacts between the two surfaces. The gas producing masks are usually designed as one size fits all, which does not conform well with the differing shape of people's facial features. As a result, the gas producing mask would not seal well and the person would not properly receive the produced gas, especially if the mask produces high pressured gas.

Therefore, there is a need for a system that has the characteristics of properly molding and sealing to the facial features of the person while effectively transferring anesthetic gas or oxygen. It is to these ends that the present invention has been developed.

SUMMARY OF THE INVENTION

To minimize the limitations in the prior art, and to minimize other limitations that will be apparent upon reading and understanding the present specification, the present invention describes an apparatus for interfacing between an gas producing mask and the person's face to ensure the correct amount of generated gas flows to the person's respiratory system without the gas leaking from the boundaries of the gas producing mask.

Generally, the invention is an airway mask interface apparatus, also known as the "interface," that is comprised of a membrane that can be placed on the middle to lower region of a person's face. The membrane may cover the person's mouth and at least part of the person's nose and allow a gas producing mask to rest on the opposite surface of the interface relative to the person's face. The surface of the interface that rests on the person's face and the surface where the gas producing mask rests are connected by a conduit system, which allows for the generated gas to flow between the gas producing mask and the person's respiratory system. The material that comprises the interface apparatus may be moldable to the shape of the person's facial features and to the contours of the gas producing mask so that the interface apparatus seals and prevents any gas produced from escaping. However, the material may also be elastic enough to restore the interface to its original shape after being detached from the person's face and the gas producing mask.

An airway mask interface apparatus, in accordance with some exemplary embodiments of the present invention, may include: a membrane having a surface that covers and substantially molds to the shape of facial features; an opposite surface, relative to the surface covering the facial features, for a gas producing mask to rest, wherein the opposite surface substantially molds and seals to the contours of the gas producing mask; and a conduit system integrated within the membrane that creates a gas passageway from the gas producing mask to a person's respiratory system.

An airway mask interface apparatus, in accordance with some exemplary embodiments of the present invention, may include: a membrane having a nasal section, an oral section, and a chin section; a surface that covers and substantially molds to the shape of facial features that contact the nasal section, the oral section, and the chin section, wherein the oral section and the chin section contain numerous fringes on the surface covering the facial features; an opposite surface, relative to the surface covering the facial features, for a gas producing mask to rest, wherein the opposite surface substantially molds and seals to the contours of the gas producing mask; and a conduit system integrated within the membrane that creates a gas passageway from the gas producing mask to a person's respiratory system.

An airway mask interface apparatus, in accordance with some exemplary embodiments of the present invention, may include: a membrane having a nasal section, an oral section, and a chin section; a surface that covers and substantially molds to the shape of facial features that contact the nasal section, the oral section, and the chin section, wherein the oral section and the chin section contain numerous fringes on the surface covering the facial features; an opposite surface, relative to the surface covering the facial features, for a gas producing mask to rest, wherein the opposite surface substantially molds and seals to the contours of the gas producing mask; a conduit system integrated within the membrane that creates a gas passageway from the gas producing mask to a person's respiratory system; and at least one inner inflatable chamber integrated within the chin section and the oral section of the membrane.

An airway mask interface apparatus, in accordance with some exemplary embodiments of the present invention, may include a supplemental gas delivery system including at least one gas containing cassette adapted to be received into a cavity within the apparatus and to provide gas to a conduit system within the apparatus thereby.

As may be appreciated by those skilled in the art, a system and device in accordance with the present invention may be utilized not only for anesthesia purposes, but also for other purposes involving the need for an interface between a person's respiratory system and a gas producing source where the prevention of gas leakage between the two bodies is necessary.

Various objectives and advantages of the present invention will become apparent from the following description taken in conjunction with the accompanying drawings wherein are set forth, by way of illustration and example, certain embodiments of this invention. The drawings submitted herein constitute a part of this specification, include exemplary embodiments of the present invention, and illustrate various objects and features thereof.

BRIEF DESCRIPTION OF THE DRAWINGS

The airway mask interface apparatus, also known as the "interface," as disclosed herein are further described in terms of exemplary embodiments. These exemplary embodiments are described in detail with reference to the drawings, which have not necessarily been drawn to scale in order to enhance their clarity and improve understanding of the various embodiments of the invention. Furthermore, elements that are known to be common and well understood to those in the industry are not depicted in order to provide a clear view of the various embodiments of the invention. These embodiments are non-limiting exemplary embodiments, in which like reference numerals represent similar structures throughout the several views of the drawings. The drawings that accompany the detailed description can be briefly described as follows:

FIG. 3 illustrates a close-up view of the interface and the different features and components the interface apparatus possesses in accordance with exemplary embodiments hereof.

FIG. 4 illustrates a close-up view of the numerous fringes on the oral and the chin section of the interface that contacts the person's face in accordance with exemplary embodiments hereof.

FIG. 5 illustrates a longitudinal cross-sectional view of the interface that runs across the nose, mouth, and chin section of the apparatus in accordance with exemplary embodiments hereof.

FIG. 6 illustrates a lateral cross-sectional view of the interface that runs across the width of the apparatus in accordance with exemplary embodiments hereof.

DETAILED DESCRIPTION OF THE INVENTION

Figure 1:
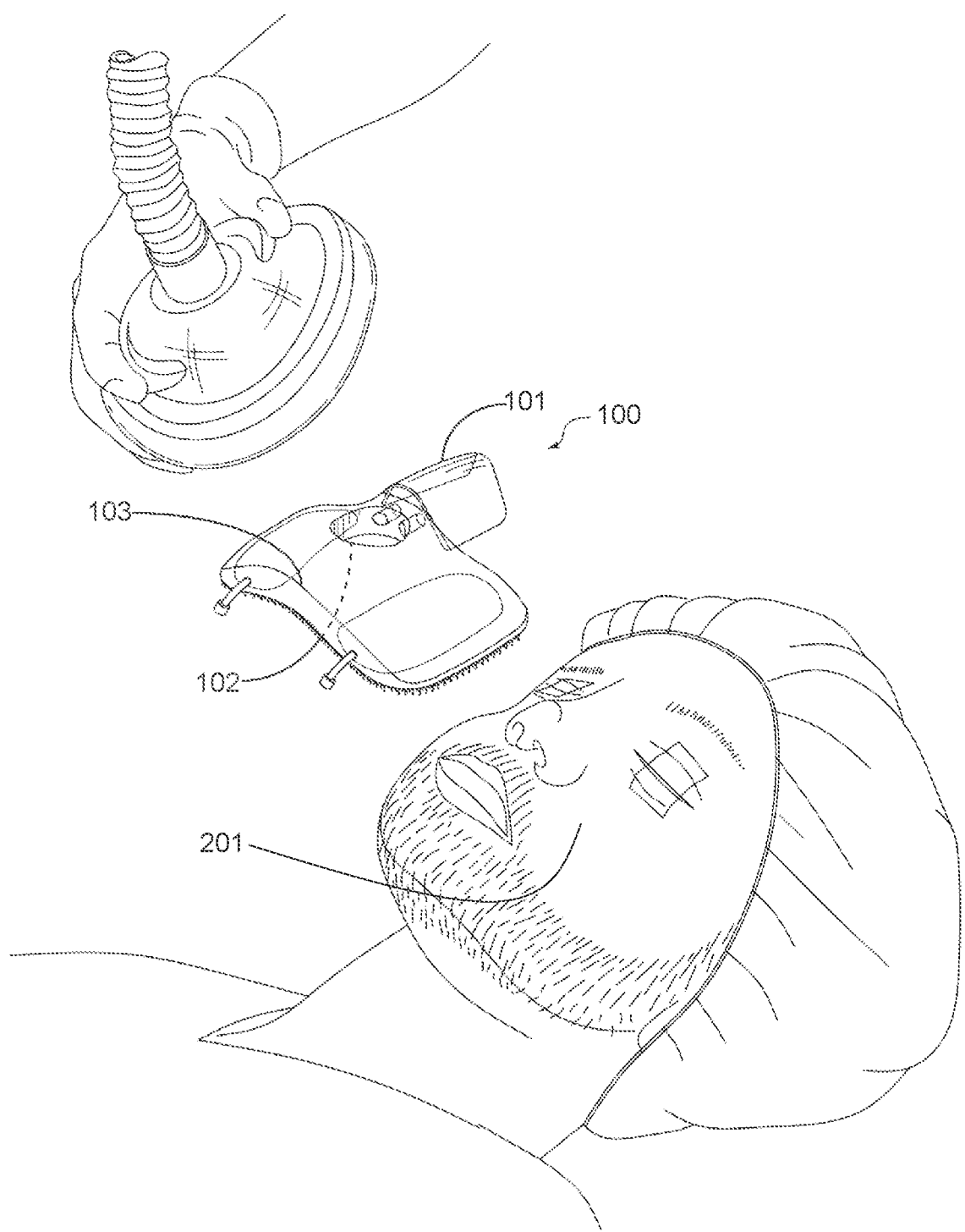
FIG. 1 illustrates an exploded view of how the interface is placed between a gas producing mask and a person's face in accordance with exemplary embodiments hereof.

In the following discussion that addresses a number of embodiments and applications of the present invention, reference is made to the accompanying drawings that form a part thereof, where depictions are made, by way of illustration, of specific embodiments in which the invention may be practiced. It is to be understood that other embodiments may be utilized, and changes may be made without departing from the scope of the invention. Wherever possible, the same reference numbers are used in the drawings and the following description to refer to the same or similar elements.

In the following detailed description, numerous specific details are set forth by way of examples in order to provide a thorough understanding of the relevant teachings. However, it should be apparent to those skilled in the art that the present teachings may be practiced without such details. In other instances, well known structures, components and/or functional or structural relationship thereof, etc., have been described at a relatively high-level, without detail, in order to avoid unnecessarily obscuring aspects of the present teachings.

Throughout the specification and claims, terms may have nuanced meanings suggested or implied in context beyond an explicitly stated meaning. Likewise, the phrase "in one embodiment/example" as used herein does not necessarily refer to the same embodiment and the phrase "in another embodiment/example" as used herein does not necessarily refer to a different embodiment. It is intended, for example, that claimed subject matter include combinations of example embodiments in whole or in part.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and or steps. Thus, such conditional language is not generally intended to imply that features, elements and or steps are in any way required for one or more embodiments, whether these features, elements and or steps are included or are to be performed in any particular embodiment.

The terms "comprising," "including," "having," and the like are synonymous and are used inclusively, in an openended fashion, and do not exclude additional elements, features, acts, operations and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require at least one of X, at least one of Y, and at least one of Z to each be present. The term "and or" means that "and" applies to some embodiments and "or" applies to some embodiments. Thus, A, B, and or C can be replaced with A, B, and C written in one sentence and A, B, or C written in another sentence. A, B, and or C means that some embodiments can include A and B, some embodiments can include A and C, some embodiments can include B and C, some embodiments can only include A, some embodiments can include only B, some embodiments can include only C, and some embodiments include A, B, and C. The term "and or" is used to avoid unnecessary redundancy. Similarly, terms, such as "a, an," or "the," again, may be understood to convey a singular usage or to convey a plural usage, depending at least in part upon context. In addition, the term "based on" may be understood as not necessarily intended to convey an exclusive set of factors and may, instead, allow for existence of additional factors not necessarily expressly described, again, depending at least in part on context.

While exemplary embodiments of the disclosure may be described, modifications, adaptations, and other implementations are possible. For example, substitutions, additions, or modifications may be made to the elements illustrated in the drawings, and the methods described herein may be modified by substituting, reordering, or adding stages to the disclosed methods. Thus, nothing in the foregoing description is intended to imply that any particular feature, characteristic, step, module, or block is necessary or indispensable. Indeed, the novel methods and systems described herein may be embodied in a variety of other forms; furthermore, various omissions, substitutions, and changes in the form of the methods and systems described herein may be made without departing from the spirit of the invention or inventions disclosed herein. Accordingly, the following detailed description does not limit the disclosure. Instead, the proper scope of the disclosure is defined by the appended claims.

The present disclosure relates generally to using an interface apparatus between a gas producing mask and the person's face to ensure that the gas or mixture of gas produced does not leak from the boundaries of the two surfaces and flows directly to the person's respiratory system.

In this disclosure, a "gas producing mask" may be an anesthesiology gas mask, an oxygen mask, or any apparatus used to generate and administer gas to a person's respiratory system. Furthermore, the term "gas" may refer to a single type of gas, such as oxygen, or a mixture of gas, such as an anesthetic gas mixture.

Turning now to the figures, FIG. 1 illustrates an exploded view of how the interface 100 is placed in between the gas producing mask and the person's face in accordance with exemplary embodiments of the present invention. The interface 100 is designed to be placed on a person's face and a gas producing mask to be placed on the opposite surface of the apparatus relative to the person's face. The interface has a nasal section 101, an oral section 102, and a chin section 103. The nasal section 101 comprises the upper portion of the interface, the oral section 102 comprises the middle portion of the interface, and the chin section 103 comprises the lower portion of the interface. Generally, the interface 100 may have any type of shape that allows the apparatus to properly cover the person's face and allow the gas producing mask to rest on the interface 100 to provide the generated gas. In an exemplary embodiment, the oral section 102 and the chin section 103 of the interface may together comprise a generally rectangular shape or an oval shape, and the nasal section 101 may comprise of a concave underneath portion so that the surface area of the interface is sufficiently large to cover at least the person's mouth and nostrils and to allow the gas producing mask to properly contact and seal with the apparatus. In an exemplary embodiment of the invention, the nasal section 101 may be elevated relative to the oral section 102 and the chin section 103 (when worn) and have a concave curvature 601 (see FIG. 6) towards the surface covering the person's face 201 in order to substantially mold to a person's shape of nose.

Figure 2:
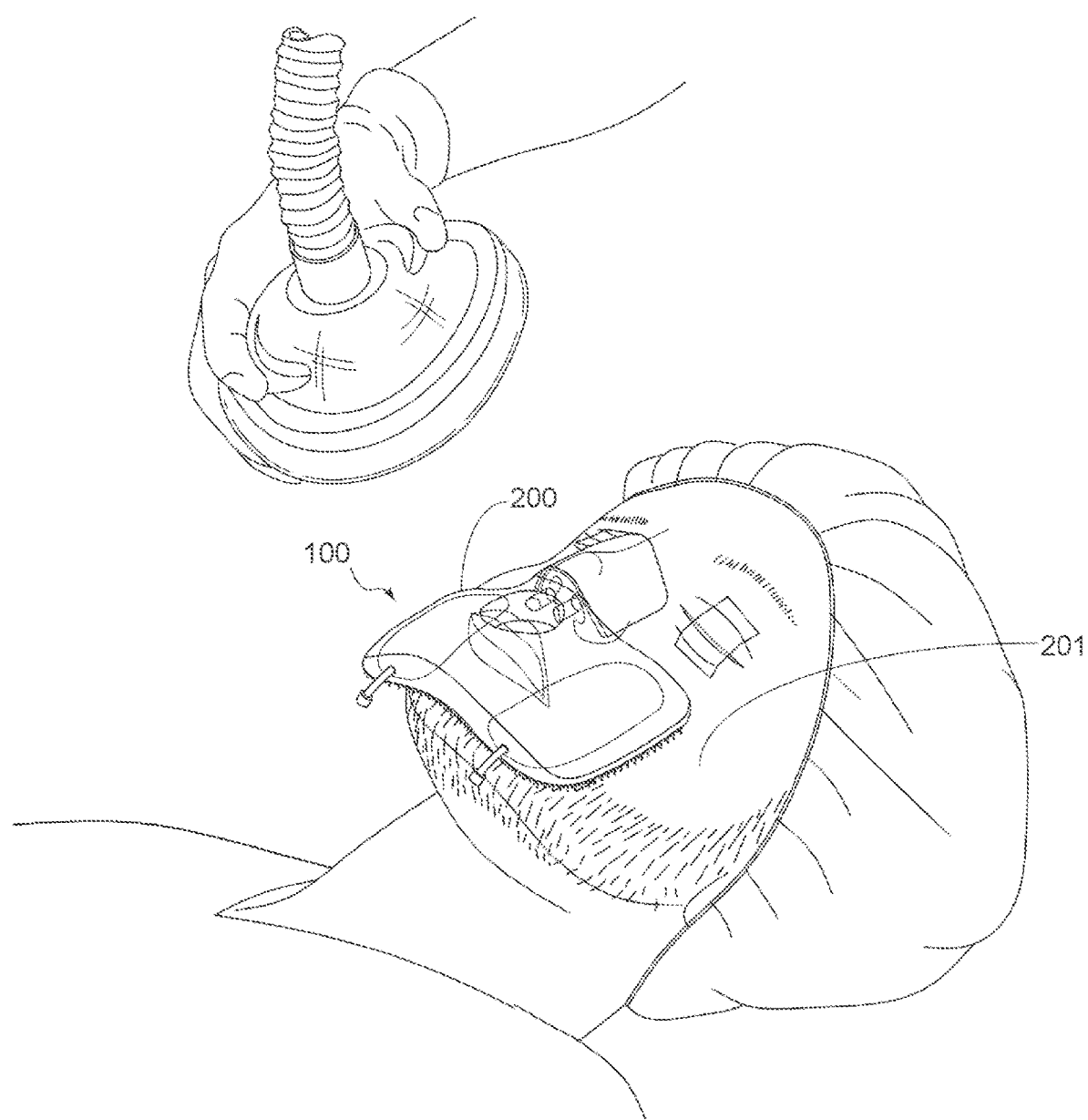
FIG. 2 illustrates the interface being placed on a person's face and covering and substantially molding to the person's facial features in accordance with exemplary embodiments hereof.

Turning now to the next figure, FIG. 2 illustrates the interface 100 being placed on the person's face 201 in accordance with exemplary embodiments of the present invention. The interface 100 may be capable of covering and molding to the person's facial features that may include, but not limited to, the nose, mouth, lips, jaws, chin, facial hair, facial skin, and/or other facial features. Generally, the interface 100 comprise of a membrane 200 capable of covering and taking the shape of a middle to lower region of a person's face 201. Without limiting the scope of the invention, the membrane 200 may be made out of a moldable polymer, such as a plastic material or a rubber material, but a person having ordinary skills in the art may use any material that covers and substantially forms to a person's facial features and the gas producing mask.

In an exemplary embodiment, an interface's surface covering the person's face 201 may substantially form (mold) with the person's facial features so that there would be little to no gaps between the two surfaces, and the gas generated would not leak from the boundaries between the two surfaces. The opposite surface of the interface relative to the person's face is the surface upon which the gas producing mask rests. The surface where the gas producing mask rests may substantially form and seal to the contours of the gas producing mask. In an exemplary embodiment of the invention, the seal created between the gas producing mask and the interface 100 prevents the generated gas from escaping from the boundaries of the gas producing mask and the interface 100. In another exemplary embodiment of the invention, the surface where the gas producing mask rests also can substantially form to the contours of the gas producing mask's gasket to substantially seal and have the same function thereby. The sealing between the interface 100 and the gas producing mask may withstand a high pressure generated by the gas producing mask.

With the molding created between the interface 100 and the person's face, and the sealing created between the interface 100 and the gas producing mask, the individual administering the generated gas can accurately administer the proper flow rate of gas to the person's respiratory system. In an exemplary embodiment of the invention, the membrane 200 that comprises the interface may be elastic enough to restore back to its original shape after the apparatus is detached from the person's face and from the gas producing mask. As a result, the same interface 100 can be reused to seal with other gas producing masks and mold with other people's facial features.

Turning now to the next figure, FIG. 3 illustrates a close-up view of the interface 100 and the different features and components the apparatus possesses in accordance with exemplary embodiments of the present invention. From this view, it may be appreciated that the interface 100 may include a conduit system 300 comprising of a primary conduit system 301 and a secondary conduit system 302 intended to create a gas pathway between the gas producing mask and a person's respiratory system.

The primary conduit system 301 allows the generated gas to flow between the gas producing mask and the person's throat. In an exemplary embodiment, the interface's 100's surface covering the person's face 201 and the surface where the gas producing mask rests are connected by the primary conduit system 301 that runs perpendicular to the two surfaces and through the oral section 102 of the apparatus. The interface 100 also may comprise a secondary conduit system 302 that connects the primary conduit system 301 to the nostrils of the person's face 201. In an exemplary embodiment, the secondary conduit system 302 may run through the nasal section 101 of the interface 100 and be orientated generally perpendicularly to the primary conduit system 301 and generally parallel to the person's nostrils. The primary conduit system 301 and the secondary conduit system 302 allow the gas produced from the gas producing mask to flow through the interface 100 and into the person's respiratory system. Generally, the primary conduit system 301 and the secondary conduit system 302 may have conduits of any shape. In one exemplary embodiment, the primary conduit system 301 and the secondary conduit system 302 may have cylindrical shaped or cuboid shaped conduits.

In another exemplary embodiment of the invention, the secondary conduit system 302 further features two nasal tubes 501 (see FIG. 5) extending outwards to connect to the person's nostrils. The nasal tubes 501 are intended to ensure that the gas flowing through the secondary conduit system 302 reaches the nasal cavity of the person and into the person's respiratory system. Generally, the tubes 501 may be of any shape. In one exemplary embodiment of the invention, the tubes 501 may have a smooth cylindrical shape or a smooth cuboid shape. In another exemplary embodiment, the terminal edges of the tubes 501 fit inside the person's nostrils and may have grooves in order to create traction between the nostrils and the tubes 501.

From FIG. 3, it may be appreciated that the interface 100 may include at least one inner inflatable chamber 303 within the membrane 200, which may be inflated and/or deflated to uniformly change the thickness of the interface 100. In one exemplary embodiment of the invention, the inner inflatable chamber 303 may be located within the chin section 103 and/or the oral section 102 of the interface 100 and around (adjacent) the conduit system 300. In another exemplary embodiment, there may be two inner inflatable chambers 303, with a first chamber 303 located on the left side of the primary conduit system 301 and a second inflatable chamber 303 located on the right side of the primary conduit system 301, with the two inner inflatable chambers 303 extending from the oral section 102 to the chin section 103. The two inner inflatable chambers 303 may be oriented symmetrically to uniformly change the thickness of the chin section 103 and the oral section 102 of the interface 100 (when inflated and/or deflated). Generally, the inner inflatable chamber 303 may have any shape. In an exemplary embodiment, the inner inflatable chamber(s) 303 may have an oval shape and/or a rectangular shape.

The inner inflatable chamber 303 may be inflated or deflated using at least one valve 305 attached to the inflatable chamber 303. The valve 305 may be connected to the inner inflatable chamber 303 via an external hose 304. In one exemplary embodiment of the invention, the valve 305 can be located on the outer boundaries of the interface 100. For example, the valve 305 can be located on the outer edge of the chin section 103 of the interface 100. Similarly, in another exemplary embodiment, the valve 305 can be connected to the external hose 304 that in turn is attached to the inner inflatable chamber 303 and placed on the outer boundaries of the interface 100. Many types of valves 305 can be used to inflate and deflate the inner inflatable chamber 303. A person having ordinary skill in the art may implement any type of valve 305 that can inflate and deflate the inner inflatable chamber 303.

Turning now to the next figure, FIG. 4 illustrates a close-up view of the numerous fringes 400 on the oral section 102 and/or the chin section 103 of the interface's 100's surface covering the person's face 201 in accordance with exemplary embodiments of the present invention. From this view and the view of FIG. 3, it may be appreciated that the interface 100 may include numerous fringes 400 to help fill in the gap between the surface covering the person's face 201 and the person's facial features that may include, but not limited to, facial hair or lax facial skin. The numerous fringes 400 can be located on the oral section 102 and/or the chin section 103 of the interface 100 around the conduit system 300 on the surface covering the person's face 201. Generally, the numerous fringes 400 may have any shape. In one exemplary embodiment of the invention, the numerous fringes 400 may have cylindrical shapes or cuboid shapes. In another exemplary embodiment of the invention, the numerous fringes 400 may be capable of substantially molding to the person's facial features, but elastic enough to restore back to their original shapes.

Turning now to the next figure, FIG. 5 illustrates a longitudinal cross-sectional view of the interface that runs across the nasal section 101, the oral section 102, and the chin section 103 of the apparatus in accordance with exemplary embodiments of the present invention.

The nasal section 101 can substantially mold and conform to differing shapes of noses or other facial features that different people may have. In one exemplary embodiment of the invention, the nasal section 101 may include a concave shape so that the interface wraps around the nasal bridge of the person. In one exemplary embodiment of the invention, the portion of the membrane 200 comprising the nasal section 101 may be thinner than the portion of the membrane 200 used in the chin section 103 and/or the oral section 102 of the interface 100.

The oral section 102 can substantially mold and conform to the differing shapes of mouths, lips, or other facial features that different people may have. The chin section 103 can substantially mold and conform to the differing shapes of chins, jaws, or other facial features that different people may have. Furthermore, the cross-sectional view of the exemplary embodiment shows numerous fringes 400 that are on the oral section 102 and chin section 103 of the interface's 100's surface covering the person's face. As mentioned before, the numerous fringes 400 are designed to help fill in the gap between the interface's 100's surface covering the person's face 201 and the person's facial features such as, but not limited to, facial hair or lax facial skin. In one exemplary embodiment, the oral section 102 of the interface 100 also may comprise a tongue holding apparatus to prevent the person's tongue from blocking the oral passageway to his or her respiratory system. As a result, the interface 100 can mold to the person's facial features that include, but not limited to, the person's nose, mouth, lips, jaws, chin, facial hair, facial skin or other facial features to disallow any gas from leaking from the boundaries of the interface 100.

FIG. 5 also shows the cross-sectional view of the primary conduit system 301 and the secondary conduit system 302 that are connected to each other and create a passageway for the produced gas to flow through the interface 100 and to the person's respiratory system. In one exemplary embodiment of the invention, the oral section 102 may contain the primary conduit system 301 and part of the secondary conduit system 302. Generally, the primary conduit system 301 and the secondary conduit system 302 may have conduits of any shape. In one exemplary embodiment, the primary conduit system 301 and the secondary conduit system 302 may have cylindrical shaped or cuboid shaped conduits. The nasal section 101 also may contain at least a part of the secondary conduit system 302. In another exemplary embodiment of the invention, the nasal section 101 may comprise of at least a part of the secondary conduit system 302 comprising of two tubes 501 extending outwards to connect to the person's nostrils.

From FIG. 5, the tubes 501 in the exemplary embodiment described above can be seen. The tubes 501 are intended to ensure that the gas flowing through the secondary conduit system 302 reaches the nasal cavity of the person and into the person's respiratory system. Generally, the tubes 501 may be of any shape. In one exemplary embodiment of the invention, the tubes 501 may have a smooth cylindrical shape or a smooth cuboid shape. In another exemplary embodiment, the terminal edges of the tubes 501 fit inside the person's nostrils and may have grooves in order to create traction between the nostrils and the tubes 501.

Generally, the interface 100 may have any type of shape that allows the apparatus to properly cover the person's face and allow the gas producing mask to rest on the interface to provide the generated gas. In an exemplary embodiment of the invention, the interface may have a chin section 103 and an oral section 102 that together form a rectangular or an oval shape that covers the person's face and has sufficient surface area for the gas producing mask to mold and seal with the interface apparatus. In one exemplary embodiment of the invention, the membrane 200 that comprises the interface is elastic enough to restore back to its original shape after the apparatus is detached from the person's face and from the gas producing mask. As a result, the interface 100 can be reused to seal with other gas producing masks and mold with other people's facial features.

Turning now to the next figure, FIG. 6 illustrates a lateral cross-sectional view of the interface 100 that runs across the width of the interface apparatus in accordance with exemplary embodiments of the present invention. From this view, it may be appreciated that the interface's nasal section 101 may be shaped in a concave curvature 601 to substantially mold with the person's nose to decrease or remove any gap that would cause the generated gas from escaping. In an exemplary embodiment of the invention, the nasal section 101 may be elevated relative to the oral section and the chin section (when worn) and have a concave curvature 601 towards the interface's surface covering the person's face 201 in order to mold to the person's shape of nose.

Figure 7:
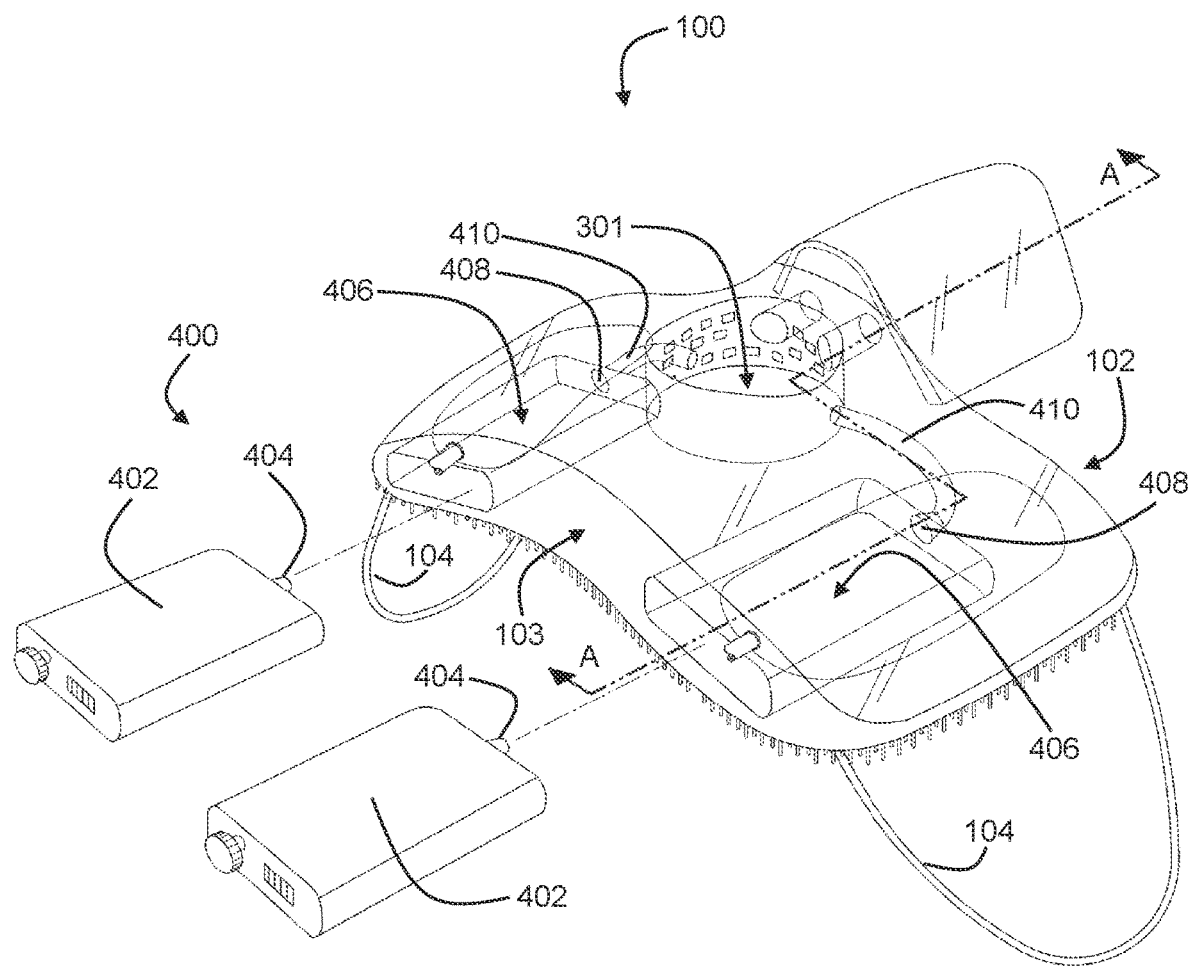
FIG. 7 illustrates a supplementary gas delivery system being configured with the interface in accordance with exemplary embodiments hereof.
Figure 8:
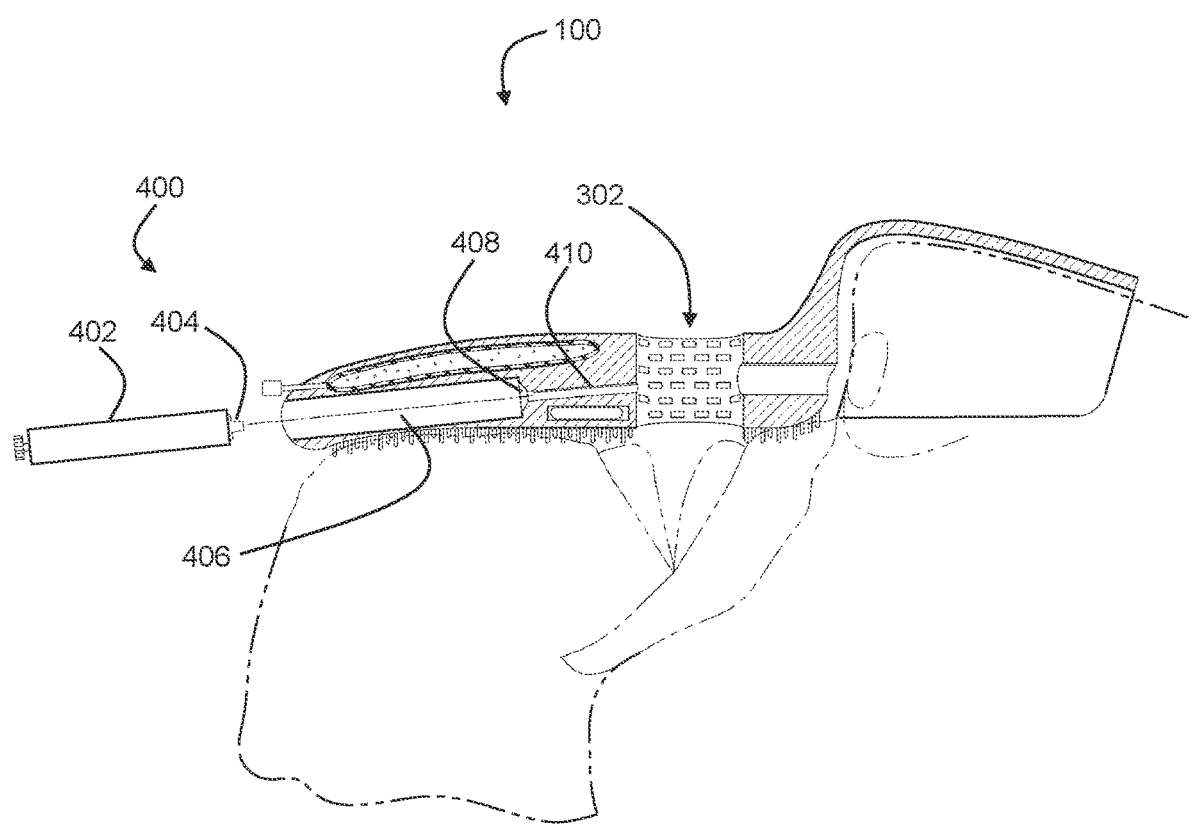
FIG. 8 illustrates the supplementary gas delivery system being configured with the interface of FIG. 7 taken from the perspective of cutlines A-A in FIG. 7.
Figure 9:
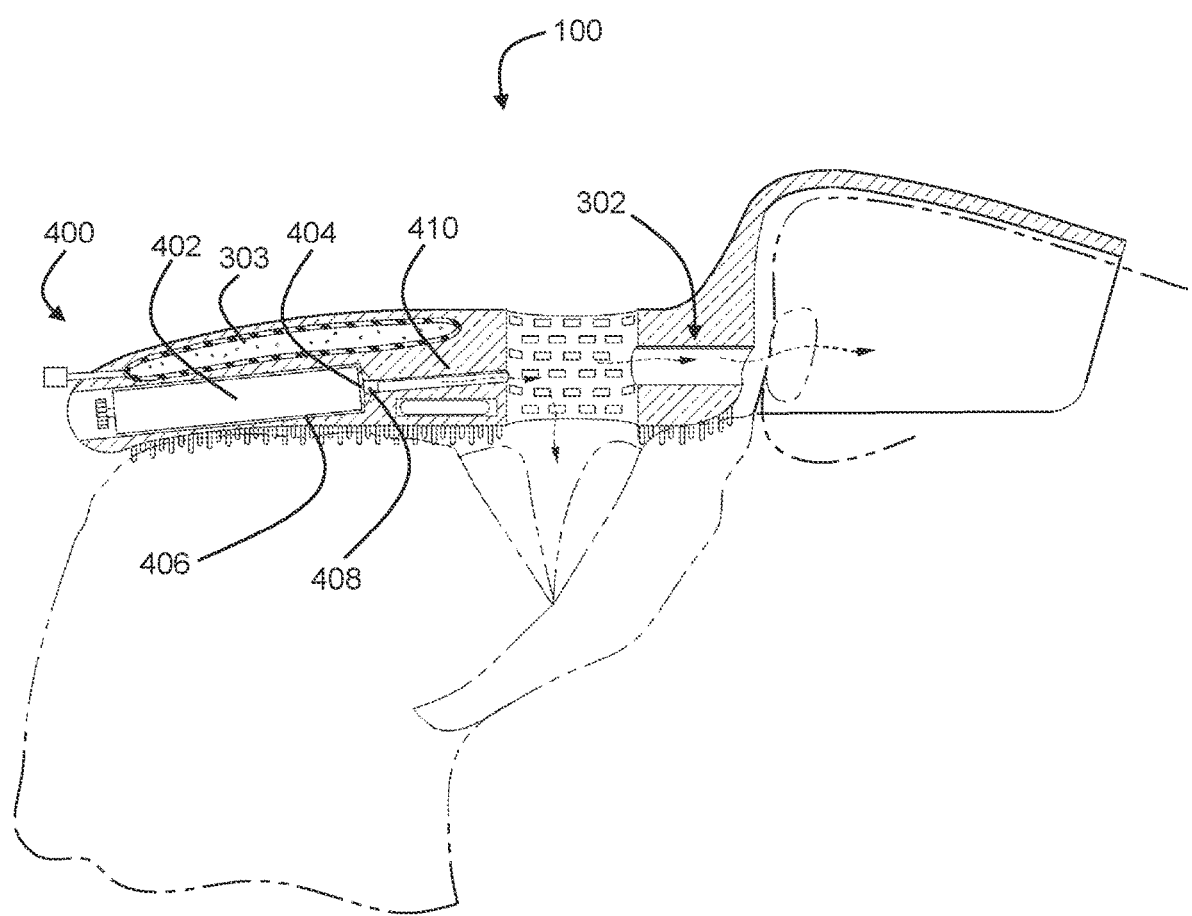
FIG. 9 illustrates the supplementary gas delivery system configured with the interface of FIG. 7 taken from the perspective of cutlines A-A in FIG. 7.

In some embodiments as shown in FIGS. 7-9, the interface 100 includes a supplemental gas delivery system 400 adapted to deliver gas to the person's respiratory system in addition to (and/or instead of) the gas being supplied by the external gas mask. In some embodiments, the supplemental gas delivery system 400 comprises one or more supplemental gas cassettes 402, each cassette 402 adapted to contain a volume of gas (e.g., pressurized oxygen) and to release a calibrated amount of the gas through a cassette output port 404 as desired. The interface 100 also includes a dedicated cassette cavity 406 for each gas cassette 402 so that the cassettes 402 may be received into and held within the interface 100 (e.g., in the interface's oral and/or chin sections 102, 103). The cassettes 402 may be held within each corresponding cavity 406 by pressure fit, detents, notches, latches, other attachment mechanisms, and any combinations thereof. FIGS. 7-8 show the cassettes 402 outside the cavities 406 and FIG. 9 shows a cassette 402 received into a cavity 406, with FIGS. 8-9 taken from the perspective of the cutlines A-A in FIG. 7.

The cavities 406 are each in fluid communication with the primary conduit system 301 (and/or the secondary conduit system 302) via gas passage tubes 410. Each gas passage tube 410 includes a first end including an input port 408 adapted to mate with the output port 404 of the corresponding cassette 402. The second end of each gas passage tube 410 terminates into the primary conduit system 301 (and/or the secondary conduit system 302) to deliver the gas thereto. In this way, gas provided by the supplemental gas delivery system 400 is adapted to engage with an input to the conduit system, the input internal to the panel, and delivered to the person's respiratory system via the interface 100.

In some embodiments, each cassette cavity 406 is sized to receive at least one cassette 402. For example, in some embodiments, the cassettes 402 may be shaped as rectangular cuboids and the cavities 406 may be shaped similarly. It is understood that the cassettes 402 and/or the cavities 406 may be formed as any suitable shapes and that the scope of the supplemental gas delivery system 400 and of the interface 100 is not limited in any way by the shapes of the cassettes 402 and/or of the cavities 406.

In some embodiments, each cassette 402 includes one or more physical control mechanisms 412 (e.g., knobs, buttons, gas level indicators, etc.) used to turn on (release gas), to adjust the level and amount of gas, to turn off, and to otherwise control the functionalities of the cassettes 402. In some embodiments it may be preferable that the control mechanisms 412 are accessible to an operator of the interface 100 when the cassettes 402 are received into the cavities 406. In this way, the cassettes 402 may be configured with the interface 100 to provide gas and may be controlled during operation. For example, as shown in FIG. 9, the control mechanisms 412 may be located on a front end of the cassettes 402 that is accessible through the front opening of a corresponding cavity 406. It also is contemplated that the cassettes 402 may be controlled by a controller (e.g., a computer) via a controller interface (wireless, cable, etc.).

In a preferred implementation as shown in FIG. 7, the interface 100 includes one cassette 402—cavity 406 combination located in the left portion of the interface 100 and one cassette 402—cavity 406 combination located in the right portion. In some embodiments as shown in FIG. 9, the cavities 406 are located beneath a corresponding inner inflatable chamber 303, however, it also is contemplated that the cavities 406 may be located above or in other locations with respect to corresponding inflatable chambers 303.

In some embodiments as shown in FIG. 7, the interface 100 includes a first ear strap 104 on its left side and a second ear strap 104 on its right side, the first and second ear straps 104 adapted to loop around that person's left and right ears, respectively, to help secure the interface 100 to the person's face 201.

In some embodiments, the combination of FIG. 1 and FIG. 2 illustrate a method for placing the interface 100 on a person's face in accordance with exemplary embodiments of the present invention. The individual administering the generated gas may place the interface 100 on the person's face by laying the surface that covers the person's face 201 on the person's face 201. In an exemplary embodiment of the invention, the interface 100 can be adjusted where the nasal section 101 covers the person's nose, the oral section 102 covers the person's mouth, and the chin section 103 covers at least a part of the person's jaws. The interface can be adjusted so that the primary conduit system 301 aligns with the person's mouth and the secondary conduit system 302 aligns with the person's nostrils to allow air flow freely through the conduit system 300 and reach the person's respiratory system.

In an exemplary embodiment, the oral section 102 and the chin section 103 may be adjusted so that the numerous fringes 400 decrease or eliminate any gaps created between the surface covering the person's face 201 and the person's face. In another exemplary embodiment, the at least one inner inflatable chamber 303 can be inflated or deflated using the at least one valve 305 to uniformly change the thickness of the interface. After the interface has been properly placed on the person's, the individual administering the generated gas may place the gas producing mask on the interface's surface where the gas producing mask rests and administer the generated gas to the person to allow the gas flow through the interface 100 and reach the person's respiratory system.

It is understood that any aspect or element of any embodiment of the interface 100 described herein or otherwise may be combined with any other aspect or element of any other embodiment to form additional embodiments of the interface 100 all of which are within the scope of the interface 100.

The foregoing detailed description has set forth various embodiments of the devices and/or processes by the use of diagrams, flowcharts, and/or examples. Insofar as such diagrams, flowcharts, and/or examples contain one or more functions and/or operations, it will be understood by those within the art that each function and/or operation within such diagrams, flowcharts, or examples may be implemented, individually and/or collectively, by a wide range of hardware, software, firmware, or virtually any combination thereof.

Those skilled in the art will recognize that it is common within the art to describe devices and/or processes in the fashion set forth herein, and thereafter use engineering practices to integrate such described devices and/or processes into other similar systems. That is, at least a part of the devices and/or processes described herein may be integrated into an airway interface system via a reasonable amount of experimentation.

The subject matter described herein sometimes illustrates different components contained within, or connected with, other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermediate components.

With respect to the use of substantially any plural and/or singular terms herein, those having skill in the art may translate from the plural to the singular and/or from the singular to the plural as is appropriate to the context and/or application. The various singular/plural permutations may be expressly set forth herein for sake of clarity.

An apparatus describing an airway device used to act as an interface between a gas producing mask and a person's face has been described. The foregoing description of the various exemplary embodiments of the invention has been presented for the purposes of illustration and disclosure. It is not intended to be exhaustive or to limit the invention to the precise form disclosed. Many modifications and variations are possible in light of the above teaching without departing from the spirit of the invention.

The invention claimed is:

1. An airway mask interface apparatus, comprising:
   a panel including an upper surface and a lower surface, the upper surface adapted to engage an output of an external gas providing mask and the lower surface adapted to engage a user's face;
   a conduit system including a first conduit and a second conduit,
      the first conduit passing through the panel from the upper surface to the lower surface and located in a position corresponding to a point of contact with a mouth region of the user's face when the panel is placed on the user's face; and
      the second conduit in fluid communication with the first conduit; and
   a supplemental gas delivery system adapted to engage with an input to the conduit system, the input internal to the panel, and
   at least one gas containing cassette configured with the panel and in fluid communication with the first conduit and/or the second conduit.

2. The airway mask interface apparatus of claim 1 further comprising at least one inflatable chamber configured with the panel between the upper surface and the lower surface.

3. The airway mask interface apparatus of claim 2 wherein the at least one inflatable chamber includes a valve mechanism adapted to inflate and/or deflate the at least one inflatable chamber.

4. The airway mask interface apparatus of claim 1 wherein the fluid communication between the at least one gas containing cassette and the first conduit and/or the second conduit is provided by at least one gas tube.

5. The airway mask interface apparatus of claim 1 wherein the at least one gas cassette includes at least one control mechanism adapted to turn on, turn off, and/or adjust a gas flow rate of gas provided by the at least one gas cassette.

6. The airway mask interface apparatus of claim 1 wherein the panel includes at least one cavity adapted to removably receive a first of the at least one gas containing cassette.

7. The airway mask interface apparatus of claim 1 wherein the panel includes a first portion located in a position corresponding to a point of contact with a chin region of the user's face when the panel is placed on the user's face, a second portion located in a position corresponding to a point of contact with a mouth and cheek region of the user's face when the panel is placed on the user's face, and/or a third portion located in a position corresponding to a point of contact with a nose region of the user's face when the panel is placed on the user's face.

8. The airway mask interface apparatus of claim 7 wherein the third portion includes a concave surface in the lower surface.

9. The airway mask interface apparatus of claim 1 wherein the second conduit includes a first tube adapted to be received into a first nostril of the user, and a second tube adapted to be received into a second nostril of the user.

10. The airway mask interface apparatus of claim 1 wherein the second conduit is substantially perpendicular to the first conduit.

11. The airway mask interface apparatus of claim 1 further comprising at least one fringe element configured with the lower surface.

12. The airway mask interface apparatus of claim 1 further comprising a least one ear strap.

13. An airway mask interface apparatus, comprising:
a panel including an upper surface and a lower surface, the upper surface adapted to engage an output of an external gas providing mask and the lower surface adapted to engage a user's face;
a first conduit passing through the panel from the upper surface to the lower surface and located in a position corresponding to a point of contact with a mouth region of the user's face when the panel is placed on the user's face; and
at least one gas cassette configured with the panel at least partially between the upper surface and the lower surface and in fluid communication with the first conduit.

14. The airway mask interface apparatus of claim 13 wherein the panel includes at least one cavity adapted to removably receive a first of the at least one gas cassette.

15. The airway mask interface apparatus of claim 13 further comprising a second conduit passing from the first conduit to a point of contact with a nose region of the user's face when the panel is placed on the user's face.

16. The airway mask interface apparatus of claim 14 wherein the second conduit includes a first tube adapted to be received into a first nostril of the user, and a second tube adapted to be received into a second nostril of the user.

17. The airway mask interface apparatus of claim 13 wherein the panel includes a first portion located in a position corresponding to a point of contact with a chin region of the user's face when the panel is placed on the user's face, a second portion located in a position corresponding to a point of contact with a mouth and cheek region of the user's face when the panel is placed on the user's face, and/or a third portion located in a position corresponding to a point of contact with a nose region of the user's face when the panel is placed on the user's face.

18. The airway mask interface apparatus of claim 17 wherein the third portion includes a concave surface in the lower surface.

19. The airway mask interface apparatus of claim 13 further comprising at least one fringe element configured with the lower surface.

* * * * *